United States Patent [19]

Tafas et al.

[11] Patent Number: 5,352,613
[45] Date of Patent: Oct. 4, 1994

[54] CYTOLOGICAL SCREENING METHOD

[76] Inventors: Triantafillos P. Tafas, 24 Bouboulinas Street, Ag. Paraskevi, Athens, Greece, 15341; Petros Tsipouras, 10 Lilac La., Farmington, Conn. 06032

[21] Appl. No.: 132,804

[22] Filed: Oct. 7, 1993

[51] Int. Cl.$^5$ .................. G01N 21/59; G01N 33/50

[52] U.S. Cl. ........................... 436/63; 436/86; 436/164; 436/174

[58] Field of Search ............. 436/63, 86, 164, 174, 436/813; 422/82.09; 356/39

[56] References Cited

U.S. PATENT DOCUMENTS

| | | | |
|---|---|---|---|
| 4,175,860 | 11/1979 | Bacus | 356/39 |
| 4,400,370 | 8/1983 | Kass | 424/3 |
| 4,523,278 | 6/1985 | Reinhardt et al. | 364/413 |
| 4,615,878 | 10/1986 | Kass | 424/3 |
| 4,675,286 | 6/1987 | Calenoff | 435/7 |
| 4,741,043 | 4/1988 | Bacus | 382/6 |
| 4,965,725 | 10/1990 | Rutenberg | 364/413.1 |
| 5,000,192 | 3/1991 | Sealfon | 128/760 |
| 5,004,681 | 4/1991 | Boyse et al. | 435/2 |
| 5,008,185 | 4/1991 | Bacus | 435/7.23 |
| 5,018,209 | 5/1991 | Bacus | 382/6 |
| 5,073,857 | 12/1991 | Peters et al. | 364/413.1 |
| 5,077,806 | 12/1991 | Peters et al. | 383/8 |
| 5,109,429 | 4/1992 | Bacus et al. | 382/6 |
| 5,153,117 | 10/1992 | Simons | 435/2 |
| 5,192,553 | 3/1993 | Boyse et al. | 424/529 |
| 5,204,884 | 4/1993 | Leary et al. | 377/10 |
| 5,252,487 | 10/1993 | Bacus et al. | 436/63 |

FOREIGN PATENT DOCUMENTS

0512965A1  11/1992  European Pat. Off. .

OTHER PUBLICATIONS

"Measuring Unconjugated Estrolin Maternal Serum to Screen for Fetal Down Syndrome", Clin Chem 38/9, 1687–1689 (1992), Cuckle.

Lockett et al., Analytical and Quantitative Cytoloty and Histology, vol. 13, No. 1, pp. 29–44, Feb., 1991.

Lockett et al., Quantitative Precision of an Automated, Fluorescence-Based Image Cytometer, vol. 14, No. 3, pp. 187–202, Jun., 1992.

Lockett et al., Automated Image-Based Cytometry with Fluoroscence-Stained Specimens, BioTechniques, vol. 10, No. 4, pp. 514–519, 1991.

Poon, et al., Automated Image Detection and Segmentation in Blood Smears, Cytometry, vol. 13, pp. 766–774, 1992.

Neuromedical Systems, Inc., The breakthrough in automated Pap smear screening, 1989/1990, 5 pages.

Parthenis et al., Blood analysis using black and white digital images, J. Biomed. Eng., vol. 14, pp. 287–292, Jul., 1992.

Abstract: Sigma Diagnostics, Alkaline Phosphatase, Leukocyte, Procedure No. 86, Oct., 1990, 4 pages.

Media Cybernetics, Image-Pro Plus Manual, pp. 6-1-2-6-13, 6-39-8-43, A-21-A-23.

Clinical Chemistry, Measuring Unconjugated Estriol in Maternal Serum to Screeen For Fetal Down Syndrome, vol. 38, No. 9, 1992, pp. 1687–1689.

The Lancet, Urea-Resistant Neutrophil Alkaline Phosphatase in Mothers with Trisomy 21 Pregnancy, Oct. 1, 1983, pp. 799–800.

The Lancet, Semi-quantitative detection of Down's syndrome with PCR, vol. 340, Sep. 5, 1992, pp. 620–621.

Prenatal Diagnosis, First-Trimester Maternal Serum Biochemical Indicators in Down Syndrome, Prematal Diagnosis, vol. 10, 1990, pp. 245–251.

Prenatal Diagnosis, vol. 11, Cu/Zn Superoxide Dismutase Quantification from Fetal Erythrocytes-An Efficient Confirmatory Test for Down's Syndrome After Maternal Serum Screening and Sonographic Investigations, 1991, pp. 295–303.

*Primary Examiner*—Nina Bhat
*Attorney, Agent, or Firm*—Wolf, Greenfield & Sacks

[57] ABSTRACT

A method and apparatus is provided, whereby the level of an intracellular analyte in a cell containing sample may be determined. The apparatus is comprised of a microscope with an X-Y stage, a video camera, a computer adapted to receive video images from the video camera, and a software program for controlling the apparatus in accordance with the method. The method provided performs digital image processing so as to cause undesired features of a video image obtained by the video camera to be diminished, while desired features are emphasized. A measurement of optical densities of desired features may then be used to determine the level of intracellular analyte.

8 Claims, 4 Drawing Sheets

CYTOLOGICAL SCREENING METHOD

FIELD OF THE INVENTION

This invention relates to methods for determining the level of an intracellular analyte in a cell-containing sample. More specifically, one aspect of the invention relates to a method for identifying pregnant women having an increased likelihood of carrying a Down syndrome-affected fetus. Another aspect of the invention relates to the detection of preleukemic states.

BACKGROUND OF THE INVENTION

The normal human complement of chromosomes consists of the sex chromosomes (designated X and Y) and 22 autosomes (numbered 1-22). It has been estimated that a minimum of 1 in 10 human conceptions has a chromosome abnormality. As a general rule, an abnormal number of sex chromosomes is not lethal, although infertility can result. In contrast, an abnormal number of autosomes typically results in early death. Of the three autosomal trisomies found in live-born babies (trisomy 21, 18 and 13), only individuals with trisomy 21 (more commonly known as Down syndrome), survive past infancy.

Although Down syndrome is easily diagnosed after birth, prenatal diagnosis is problematic. To date, karyotyping of fetal cells is the only definitive method for diagnosing the disorder. Typically, fetal cells for karyotyping are isolated by invasive procedures such as amniocentesis or chorionic villus sampling. Amniocentesis and chorionic villus sampling are performed at about 15-18 weeks and 9-12 weeks gestation, respectively. A fetal loss rate of about 0.2-0.5% is associated with amniocentesis; Chorionic villus sampling reportedly has a fetal loss rate of between about 1-2%.

The finite risks of miscarriage of a normal fetus, as well as the high costs associated with the above-described procedures, have limited the widespread application of amniocentesis and chorionic villus sampling for the routine screening of pregnant women. Thus, diagnosis of Down syndrome during pregnancy has been limited to women identified as having a high risk for carrying a Down syndrome-affected child. In practice, this has meant limiting the tests for Down syndrome to women who are age 35 and older or who have a history of pregnancies associated with chromosomal damage. Approximately 20% of Down Syndrome children are born to women 35 years old or older.

In view of the relatively high incidence of Down syndrome infants born to women age 35 and under, efforts have been made to develop screening procedures to identify women having an elevated risk of carrying a Down syndrome-affected child. These methods include sonography and/or the measurement in maternal blood of multiple markers indicative of a Down syndrome pregnancy.

The association of various maternal serum markers with Down syndrome has been reported. In general, the absolute concentration of a marker is not determined. Rather, the amount of marker is expressed as a multiple of a normal (i.e., non-Down syndrome pregnancy) median ("MoMs") at a known gestation time. Thus, the average MoM value for a marker indicates the extent of marker increase or decrease for a Down syndrome pregnancy compared to a normal pregnancy.

A comparison of the ability of twelve markers to distinguish a Down syndrome pregnancy from a normal pregnancy has been reported (Cuckle, H., *Clin. Chem.* 38(9):1687 1689 (1992). The ability of different markers to distinguish a Down syndrome pregnancy was based upon a determination of the number of standard deviations from which each marker MoM valve for a Down syndrome pregnancy differed from the MoM value obtained for a normal pregnancy. The most discriminating markers reportedly were neutrophil alkaline phosphatase, chorionic gonadotropin (hCG) and free-beta-hCG, with alpha-fetoprotein (AFP), $\mu$Ec (unconjugated estriol) and pregnancy-specific beta$_1$-glycoprotein. However, the author further concluded that in practice, hCG (intact, total, or free-beta) was the marker of first choice because the cytochemical assay of neutrophil alkaline phosphatase is not suitable for large throughput of samples.

The term "cytochemical assay" refers to a method for studying the presence and/or distribution of intracellular components. In general, this is accomplished by contacting a plurality of fixed cells with a stain or other reagent to yield a visually-detectable product. In the cytochemical assay of neutrophil alkaline phosphatase, a blood sample smear is fixed, lysed and bound with a substrate of the enzyme to give an insoluble product which appears as colored granules in the cytoplasm of neutrophils. Each step of the assay is labor-intensive and involves a high degree of subjectivity. Thus, for example, a laboratory technologist must manually prepare and stain the blood sample smear, visually select neutrophils from other cells in the optical field, assess the amount of color present in the stained cells and compare this visually-perceived amount of color to the color of control blood smears having amounts of neutrophil alkaline phosphatase indicative of the presence or absence of a Down syndrome pregnancy. It will be readily apparent that the above-described procedure is quite time-consuming. Indeed, it may take 10-15 minutes to perform this assay on one cell sample from one individual.

Although cytochemical assays for the classification of blood cells have been automated to some extent (see e.g., Parthenis, K. and Metazaki-Kossionides, C., *J. Biomed. Eng.* 14:287-292 (1992) and Pooh, S., et al., *Cytometry* 13:766-774 (1992)), automated cytochemical analysis has not been applied to the quantitation of intracellular analytes for the identification of pregnant women having an elevated likelihood of carrying a Down syndrome-affected fetus.

However, automated cytochemical analysis has not been applied to the quantitation of other intracellular analytes, because of the difficulty encountered in isolating the particular cells or cell structures of interest within a cell sample. Consider, for example, the assay of neutrophil alkaline phosphatase discussed above. The optical field viewed by the Technician includes red blood cells, debris and other objects, as well as the sought-after neutrophils. Furthermore, denser portions of a smear can include overlapped or clumped objects that appear to be single objects.

Therefore, it is a general goal of the present invention to provide a method and apparatus for performing cytochemical analysis in order to quantify the level of an intracellular analyte within selected cell types which can be found within a cell sample.

A more particular goal of the present invention is to provide a method and apparatus suitable for performing automated cytochemical analysis for quantifying the level of intracellular analytes suitable for identifying preleukemic states and pregnant women having an elevated likelihood of carrying a Down Syndrome-affected fetus.

Another goal is to provide a method of automatically isolating one image object within an optical field containing a variety of types of image objects, some of which are of interest.

SUMMARY OF THE INVENTION

According to one aspect of the present invention, a method is provided for determining the level of a target substance in a cell-containing sample. As used herein, the target substance can be a chemical or chemical product found within the cells of the cell-containing sample, or the target substance can be a structure or other biological entity within the cells of the cell-containing sample. According to another aspect of the present invention, a method is provided for determining the level of an intracellular analyte indicative of an elevated likelihood that a pregnant woman is carrying a Down syndrome-affected fetus. For example, the method can be used to determine the level of alkaline phosphatase in neutrophils present in maternal serum.

According to one method, a plurality of cells from a cell-containing sample supported on a microscope slide or other support is placed in an optical path of an image detector. The plurality of cells can contain a target substance such as alkaline phosphatase, to which a reagent for optically indicating the presence of the target substance has been applied. For example, the reagent can be a simple stain or can be a substrate which reacts with the target substance to produce an optical change. The image detector can be a microscope equipped with a video camera. An image of the optical field is thus obtained. The image can be stored or communicated as an array of points having optical density values. The array of points can be any suitable digital storage array containing values of optical densities measured at points corresponding to those obtained by dividing the optical field into a rectilinear grid. The optical density values can include color information, such as separate optical density values for red, green and blue. The obtained image is then filtered so as to sharpen certain desireable aspects of the image and simultaneously to de-emphasize unneeded features. This can be performed by a "closing" filter, for example. A parameter set within which an image object of interest fits is defined. The image object of interest can be a particular cell type, for example neutrophils. Image objects conforming to the defined parameter set are then selected. Finally, the optical densities of points within the selected image objects are compared with a predetermined scale.

BRIEF DESCRIPTION OF THE DRAWING

Like reference numerals represent like elements in The accompanying figures, in which.

DETAILED DESCRIPTION

Figure 1:
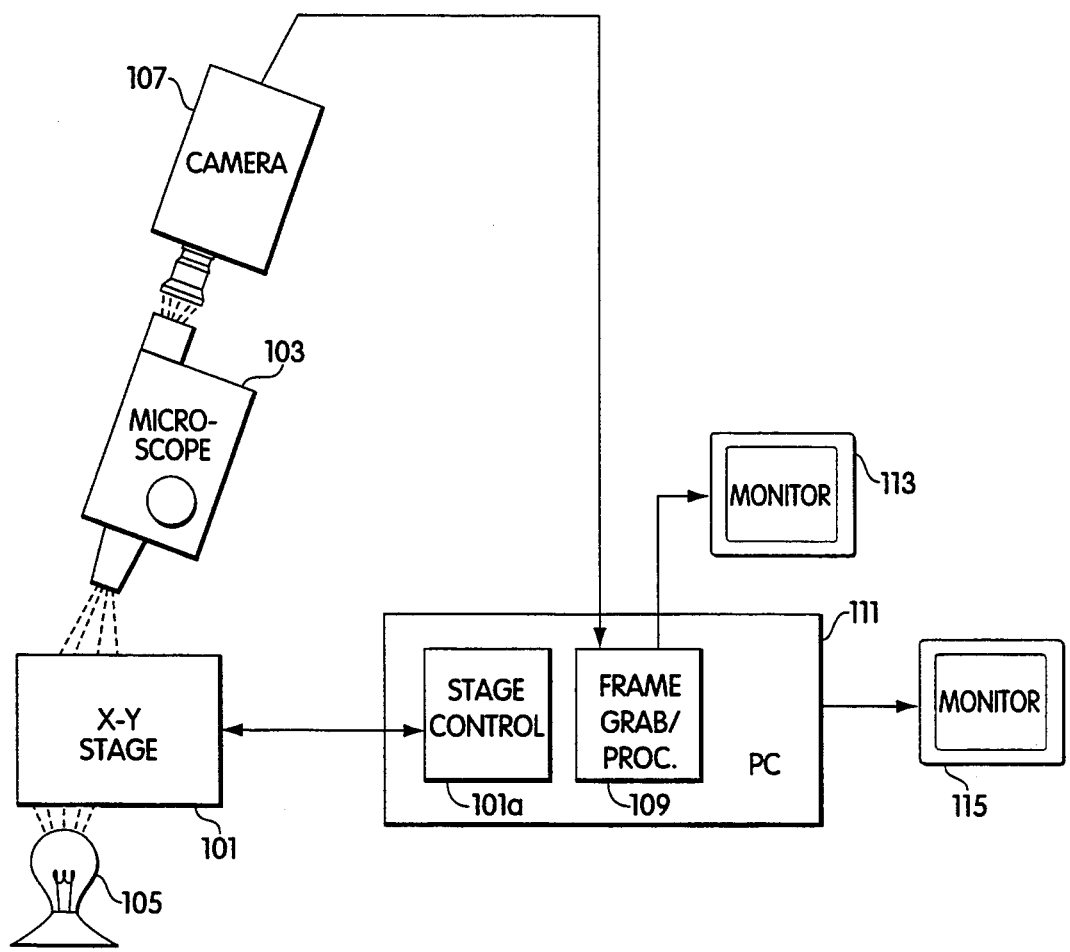
FIG. 1 is a block diagram of a system according to one embodiment of the present invention.

The present invention can be better understood by reading the following detailed description of one embodiment thereof, in connection with the figures.

Measurement of activity of the urea resistant neutrophil alkaline phosphate (UREA-NAP) using an automated imaging method.

REAGENTS;

The following solutions are used in the following protocol.

Solution 1:

Solution 1 was prepared by mixing 9 volumes of methanol (absolute methanol, Sigma Chemical Corporation, St. Louis, MO, product #17-5) and 1 volume of buffered formalin (10% solution, Sigma Chemical Corporation, St. Louis, MO, product #HT 50 1-1). Solution 1 was cooled to $-20°$ C. before use and was stable for up to 7 days. The fixative should be prepared at least weekly, kept at $-20°$ C. and well mixed immediately before use. Slides that are fixed with warm fixative show reduced activity. Failure to adequately wash fixative from slides also reduces activity. The fixed slide can be assayed immediately or stored at about $-20°$ C. until assay. In general, unwanted cell removal from the slides during wash steps is attributable to an error in the pH of the urea solution (described below) or to the use of outdated fixative. Accordingly, care must be used in accurately preparing and storing the reagents described herein.

Solution 2:

Solution 2 contains 1.5M urea (Ultrapure Urea, Gibco-BRL, Gaithersburg, MD, Catalog No. 5505.UA) in 0.1 M Tris buffer (Sigma Chemical Corporation, St. Louis, MO, product T-1503). Solution 2 was prepared by mixing 90 g urea, 12.12 g TRIS (hydroxymethyl aminomethan) and 24 ml 4M HCl and making up to 1 liter with distilled water. The pH was adjusted to pH 7.4 before use. Solution 2 was stable for up to about 2 months when stored at 4° C. in a dark bottle. However, it is recommended that fresh solution is prepared once a month.

The pH of the urea solution is important and should be checked frequently. A Copelin jar or other container suitable for immersing slides should be used for treating slides and filled daily with fresh solution. The slides may be held either upright or laid flat for immersion.

Solution 3:

Solution 3 is prepared by adding 1 mg of naphthol-AS biphospate salt (SIGMA Catalogue #N 2250) and 8 mg of fast red violet LB salt (SIGMA Catalogue #F 3381), in 10 ml of stock solution. The solution should be filtered before use. The stock solution is prepared by adding 2.625 gm of 2-amino-2-methyl-1,3-propanediol (Merck Catalogue #801464), in 125 ml of distilled and deionized water. Finally, add 35 ml of 0.1N HCl (SIGMA Catalogue #210-4) and sufficient distilled and de-ionized water to form a final volume of 500 ml. Solution 3 is kept at 4° C. up to 2 months.

Solution 4:

Solution 4 is Mayers Hamalum solution (Merck Catalogue #9249).

A Sample Preparation:

(1) Preparation of the Blood Smear:

The blood smear is prepared according to standard procedures known to one of ordinary skill in the art. An exemplary protocol is disclosed herein.

Venous blood was obtained by venipuncture or finger stick and was anti-coagulated by heparin.

For the identification of women having an elevated likelihood of carrying a Down syndrome-affected fetus, the blood sample was obtained between approximately 15 and 17 weeks gestation. One or two drops of blood are spread on a glass slide, fixed for one minute by immersion into a methanol/formalin solution ("Solution 1"), washed in distilled and deionized water (for 30–60 seconds) and allowed to air dry.

Unfixed slides are stable for 1–2 days at room temperature, however some loss of activity can occur after this time. If staining will be delayed more than 2 days, the unfixed slides should be placed back to back (so the films are not damaged) in a blue slide carrier, wrapped in parafilm "M" (American National Cay, Greenwich, Conn.) so that the carrier is airtight, and stored at freezer temperatures.

The slides were allowed to warm to room temperature before unwrapping. Failure to allow the slides to warm prior to unwrapping results in the formation of condensation which causes lysis of the unfixed smear. Care should be used to avoid touching the films with fingers since the cells contained on the slides are easily damaged.

(2) Urea Treatment:

The fixed blood smear was immersed for 15 minutes at 37° C. in "Solution 2". Following the urea treatment, the slides were washed in running water and allowed to dry.

(3) Staining:

Following the urea treatment, the slides were incubated with a freshly prepared working solution ("Solution 3") of naphthol AS-biphosphate salt and fast red violet LB at 37° C. for 15 minutes by piperting approximately 1 ml of Solution 3 into a square petrie dish and placing the slides (smear side down) on top of the pool of substrate with one end of the slide supported by a glass capillary tube. The petrie dish containing the slide was floated in a 37° C. water bath during the incubation period, washed briefly in tap water, and counterstained with aqueous hematoxylin ("Solution 4") for five minutes. The slides were thoroughly rinsed in tap water and allowed to dry prior to sample analysis. Solution 3 should be prepared immediately before use.

B. Sample Analysis:

The presence of Urea Resistant Alkaline Phosphatase, found principally in mature neutrophils, was demonstrated by the azo-dye coupling technique, which depends upon the hydrolysis of a substrate containing Alpha Napthol Phosphate. As hydrolysis occurs, the liberated napthol couples to a diazotized amine and forms an insoluble colored precipitate. The intensity of the precipitate is a rough measure of the enzyme content of individual cells. Enzyme activity is maximal at pH 9.0–10.0.

Alkaline phosphatase activity was indicated by a precipitate of red granules. Scoring was based on the intensity of staining and the number and size of red granules in the cytoplasm of the neutrophils. One hundred neutrophils on each slide were individually scored according to the intensity of the staining of the cytoplasmic granules. Grading of the granules was based on the scale proposed by Cuckle et al. (*Br. Med. J.* 301:1024–1026 (1990) (described below). Briefly, a scale grade of 0 was assigned when there were no granules present and the stain was absent or faint; grade 1 was assigned in the presence of a few scattered granules and the stain was pale pink; grade 2 was assigned in the presence of many regularly dispersed granules and the stain was moderately pink; grade 3 was assigned when numerous granules throughout the whole of the cytoplasm were observed and the stain is dark pink to red. The sum of the scores of 100 cells was regarded as the "score" for a given blood smear.

With the use of a 100× oil immersion lens, 100 consecutive neutrophils were counted in the area of ideal thickness, and preferably where the erythrocytes just touched each other and were scored (i.e., assigned a UREA-NAP grade) between 0 and 3 as described above.

Additionally, the cells were automatically rated using digital imaging system disclosed herein.

C. Automated Sample Analysis:

Automated sample analysis is performed by an apparatus and method capable of distinguishing in an optical field, objects of interest from other objects and background, collectively called background. Furthermore, once an object of interest has been identified, the optical density of points within that object, or other parameters of interest relative to that object can be measured and stored.

(1) Apparatus:

An apparatus according to one embodiment of the present invention is now described in connection with FIG. 1. The block diagram of FIG. 1 shows the basic elements of a system according to this embodiment.

The basic elements of the system include an X-Y stage a light source 105, a microscope 103, a camera 107, a specially-equipped personal computer (PC) 111, and one or two monitors 113 and 115. The individual elements of the system can be custom-built or purchased off-the-shelf as standard components. These elements will now be described in somewhat greater detail.

The X-Y stage 101 can be any positionable stage suitable for use with microscope 103. For example, X-Y stage 101 can be a manually positioned stage having conventional micrometer adjustments for positioning of a microscope slide by a human operator. Alternatively, X-Y stage 101 can be an electrically controlled device, controllable by the PC 111, for example. Such an electrically controlled X-Y stage 101 can therefore further include a stage controller circuit card 101a, to be plugged into an expansion bus of a personal computer 111. Electrically controlled stages, such as described here, are produced by microscope manufacturers, including Zeiss (Berlin, Germany), and other manufacturing concerns, such as Macton Dynamics, Inc. (Horsham, Pa.).

The microscope 103 can be a conventional, oil immersion microscope having a 100× objective lens. For example, The Zeiss standard microscope, equipped with a 100× objective lens and providing a total magnification between 600×–1,000× is suitable. The microscope 103 and stage 101 are set up include a controlled light source 105, capable of providing consistent and even illumination of an image field viewed through the microscope 103.

The image is viewed by a camera 107. The camera 107 can be any color or monochrome video camera adapted for connection to the microscope 103. The preferred camera 107 is a Javelin (Torrance, CA, model no. JE3642X). The Javelin camera is a color camera having a resolution of 480×640 pixels. Furthermore, the Javelin camera 107 has a sensitivity of 480 TVL. The output of camera 107 is fed to a frame grabber and image processor circuit board 109 installed in the PC 111.

The frame grabber 109 can be, for example, a Targa Plus board, available from True-Vision (Indianapolis, IN). The Targa Plus frame grabber 109 supports display to a dedicated monitor 113. While it is not required that multiple monitors be provided, the embodiment described herein does include a dedicated monitor 113. Any monitor suitable for use with the Targa Plus frame grabber 109 can be used. In this embodiment the dedicated monitor 113 is a Mitsubishi (Nagasaki, Japan) multi-sync monitor.

In order to have sufficient processing and storage capabilities available, the PC 111 can be any Intel 486-based PC having at least 4 MB RAM and at least 200 MB of hard disk drive storage space. The PC 111 of the present embodiment further includes a monitor 115. Other than the specific features described herein, the PC 111 is conventional, and can include keyboard, printer, or other desired peripheral devices not shown.

(2) Method:

The PC 111 executes a software program called Image-Pro Plus, which controls operation of the frame grabber 109 and the processing of images captured by frame grabber 109 and subsequently stored in PC 111 as disk files. Image-Pro Plus is readily available from Media Cybernetics (Silver Spring, MD). It provides specialized routines particularly suitable for performing such image processing tasks as filtering, object selection and various measurement functions. In order to process images using Image-Pro Plus, a number of system calibration steps must first be taken.

Figure 2:
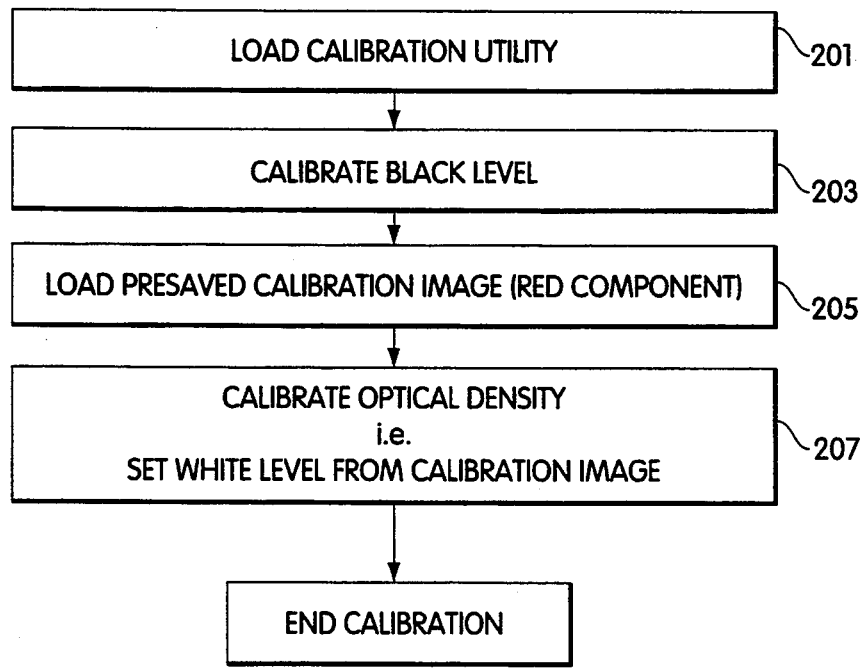
FIG. 2 is a flow chart representing the steps of a calibration method according to one aspect of the present invention.

The flowchart of FIG. 2 shows the calibration steps of this embodiment of the present invention. Calibration permits the software to compensate for day-to-day variations in performance, as well as variations from one microscope 103, camera 107, etc. to another. Calibration establishes the minimum image block level, the maximum image white level and the image magnification.

In step 201, the Image-Pro Plus calibration utility is loaded into the PC 111 for execution. The black level is next established (step 203). A tagged image file format (TIFF) file containing an image of the visual field seen by the camera 107 and microscope 103 with light 105 turned off is loaded into RAM in the PC 111. A point within this image is then manually selected, using means provided by Image-Pro Plus, and identified as the minimum white level to be expected. Next, (step 205) a typical image of a cell sample having a high light intensity in the inter-cell regions is loaded into RAM in the PC 111. One of the high intensity inter-cell regions is identified as representing the maximum white level to be expected. At this point, the light source 105, microscope 103 and camera 107 variations as to light intensity are adequately calibrated.

A standard microscope calibration slide or other solid support (e.g., culture plate or well) having known, fixed distances marked thereon is then viewed through the microscope 103 and camera 107. This image is captured to a TIFF file, which is subsequently loaded into RAM in the PC 111. An operator then designates a correspondence between a span measured in pixels in the TIFF file and an actual distance marked on the calibration slide. The optical magnification due to the microscope 103 and camera 107 is thus calibrated.

The system is now calibrated to perform the automated analysis.

Figure 3:
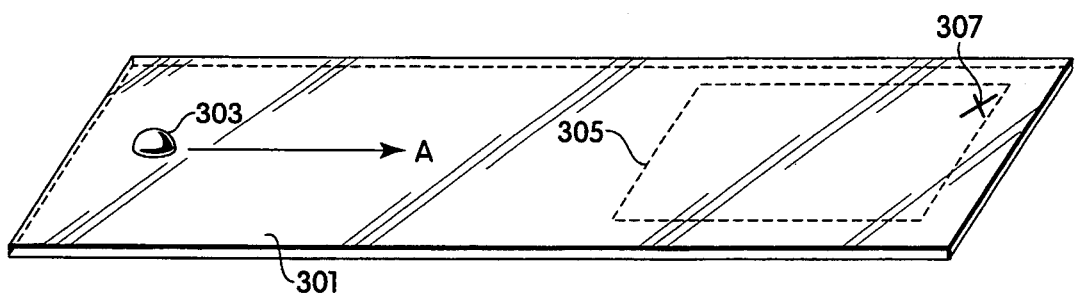
FIG. 3 is a top view of a microscope slide showing a blood smear thereon.

A slide containing a blood smear prepared according to the Example protocol, such as shown in FIG. 3 is loaded onto X-Y stage 101. As seen in FIG. 3, if a drop of blood 303 is placed near the left side of slide 301 and smeared in direction A, then the area of best observation 305 lies near the end of the smear, because the density of cells decreases in direction A, so as to result in nearly a single layer of cells in the area of best observation 305. Therefore, observations will be in from a point 307 at one corner of the area of best observation 305. Point 307 is therefore the initial observation position.

The high level operation of the automated analysis program is now described in connection with FIG. 4.

After calibration (step 401), the X-Y stage 101 is moved to the initial observation position 307 (step 403). Finally, the processing loop (steps 405, 407 and 409) is executed repeatedly until either a predetermined number of cells of a particular type have been identified and measured or the entire area of best observation 305 has been analyzed. In the application for which the present embodiment is intended, identifying neutrophils containing high levels of alkaline phosphatase, the loop would preferably be executed until 100 neutrophils have been measured and data representing the measurements have been stored in an ASCII file.

Execution of the processing loop is controlled by loop parameter M (step 405). The loop parameter M represents the number of rows of non-overlapping optical fields perpendicular to direction A within the area of best observation 305. When the processing loop has been executed M times, the program ends execution. If the entire best observation area 305 is analyzed, but data for fewer than 100 neutrophils have been stored in the ASCII file, then the analysis terminates with an indication that insufficient neutrophils were found.

After each execution of the main processing procedure (step 407), the slide is moved in a direction perpendicular to A (step 409). Control then returns to check the loop parameter M (step 405).

Figure 5:
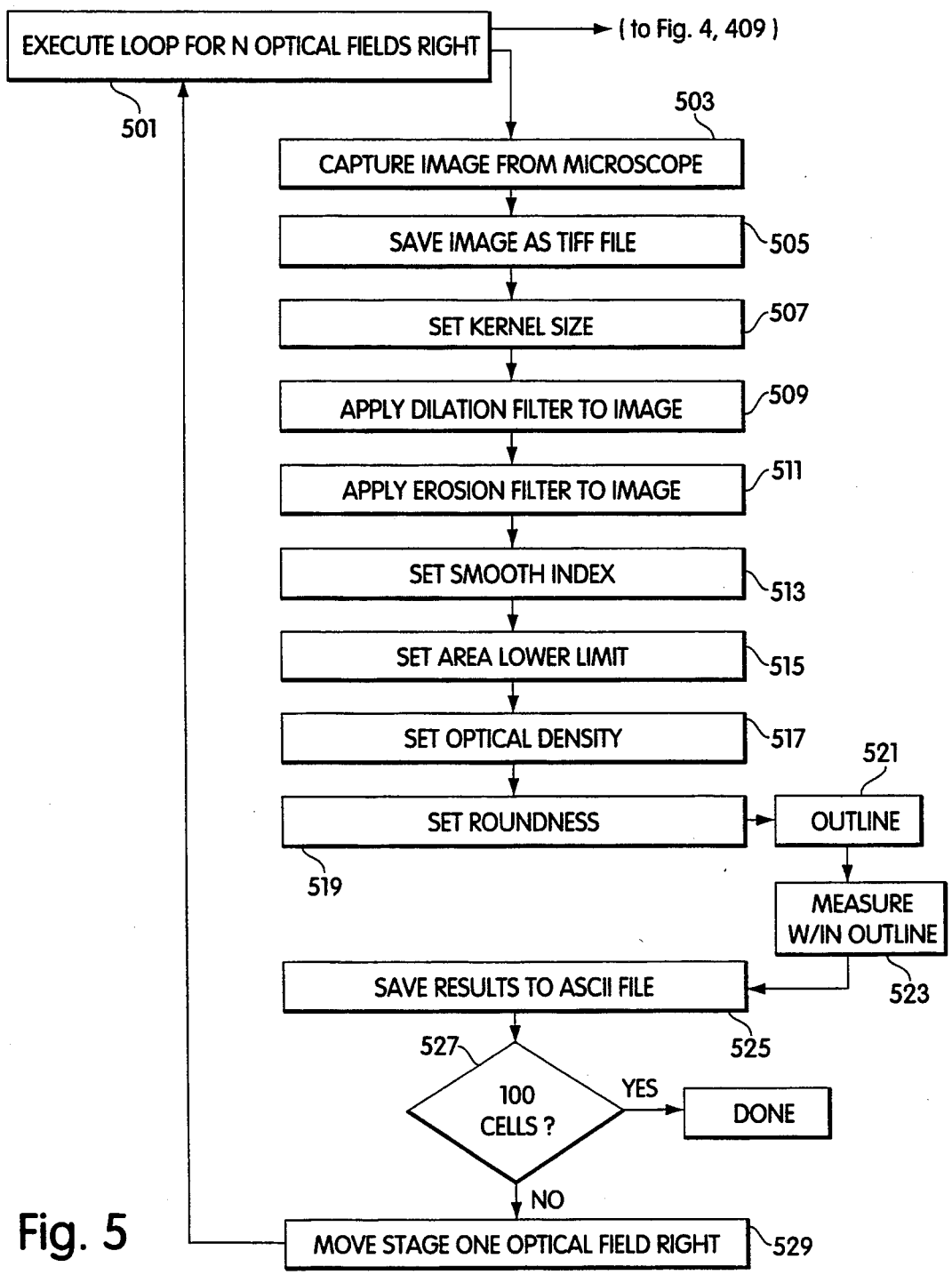
FIG. 5 is a flow chart representing the steps of a main processing procedure of the method of FIG. 4 according to one aspect of the present invention.

The main processing procedure (step 407) is now described in greater detail in connection with FIG. 5.

The following steps are repeated as an iterative loop, in accordance with loop parameter N (step 501). The loop parameter N represents the number of non-overlapping optical fields in direction A of the area of best observation 305. First, frame grabber 109 is instructed to capture an image from microscope 103 and camera 107 (step 503). Next, the captured image is saved as a TIFF file (step 505). Processing of the captured image contained in the TIFF file can now begin. In accordance with this illustrative embodiments, only the red optical densities in the TIFF file are used in the subsequent processing. In the present application of analyzing a stained target chemical in blood, this has provided the best contrast yielding high quality results, In step 507, the Image-Pro Plus filter kernel is set to the 7×7 size. The odd kernel sizes 5×5, 7×7 and 11×11 are approximately circular, within the limits of their resolution. Circular kernels are preferable for filtering cell shapes. Larger objects within an image are better filtered by larger kernel sizes. For a 1000× magnification (10× ocular times 100× objective) by the microscope 103 of a blood sample, the kernel size of 7×7 has been found experimentally to be optimum. The selected kernel is now used to apply a closing filter to the image (steps 509 and 511). A closing filter "closes" small dark holes in an otherwise bright image. Thus, it has the effect of enhancing the difference between objects in the image and the background of the image. The closing filter is implemented in two stages. First, a dilation filter (step 509) is applied to the image. The dilation filter replaces the center pixel value in the kernel with the value of the brightest pixel in the kernel. In the second stage, an erosion filter (step 511) is applied to the image. The erosion filter replaces the center pixel value with the darkest pixel value in the kernel. The closing filter has been found to be all the image pre-processing required for proper operation of the present invention.

Any neutrophils which appear in the image resulting from filtering the TIFF file can now be identified by Image-Pro Plus on the basis of their morphological characteristics (steps 513, 515, 517 and 519). When Image-Pro Plus selects an object, the object is identified as being that portion of an image within a defined boundary. Therefore, in order to have Image-Pro Plus define boundaries of a proper complexity with respect to the actual cell outline of a neutrophil, the "smoothing index" is set to the value 2 (step 513). The smoothing index value used in this illustrative embodiment is an arbitrary value which has been determined empirically to provide satisfactory operation. Since neutrophils are relatively larger than the other objects likely to be found in the image, a minimum area for selected objects is set (step 515). In the case of the present embodiment, a minimum area of $1 \mu m^2$ has been found to satisfactorily separate the neutrophil from most small background objects, and debris. Red blood cells, clumped red blood cells and other large low optical density items found in a sample can be excluded by setting a minimum optical density, which selected objects must exceed (step 517). Finally, objects are selected on the basis of having a roundness value between approximately 1 and 3 (step 519). For an object having a perimeter length P and an area A, the roundness is obtained by $P^2/4\pi A$. Thus, a circular object has a roundness of 1, while an object having a roundness of 3 is somewhat elliptical. Clusters, or clumps of cells which often occur in blood smears nearly always have a roundness outside of the selected limits.

Figure 4:
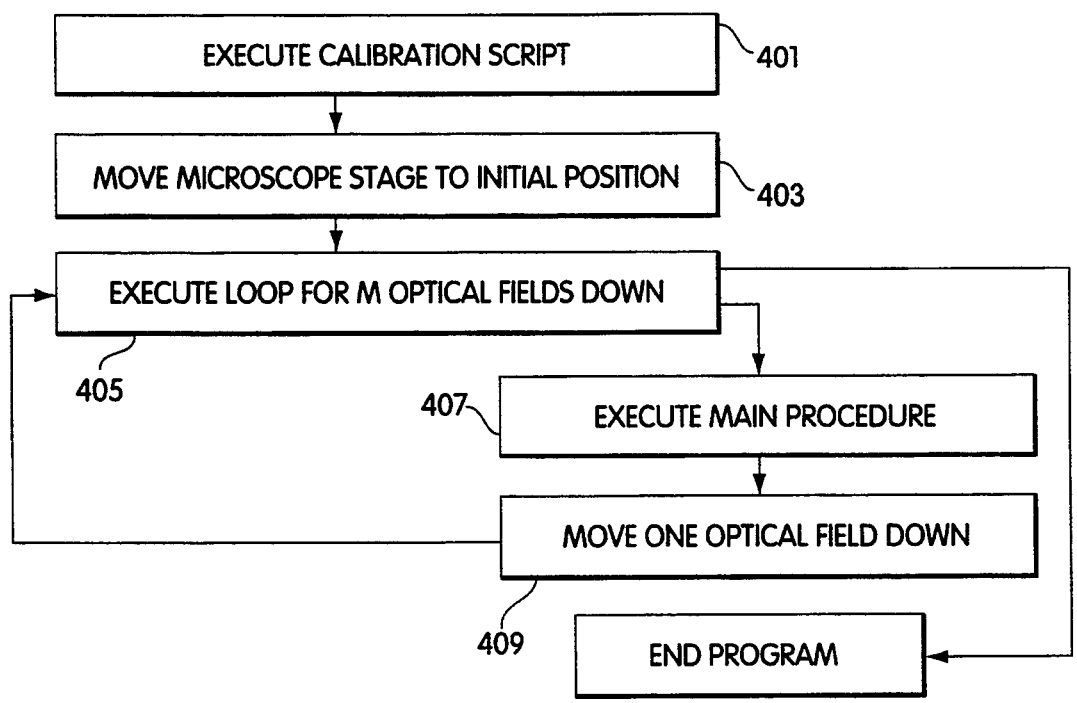
FIG. 4 is a flow chart representing the steps of a method according to one aspect of the present invention.

It should be noted that although the present embodiment sets the parameters with each execution of the main processing procedure, these could alternatively be set at some earlier point in processing, such as during calibration (FIG. 4, step 401).

Objects can now be selected, measured and counted (steps 521, 523, 525 and 527). First, objects conforming to the selected parameters are outlined (step 521). Once the outline has been drawn, any desired parameters can be measured within that outline. Thus, in the present embodiment, the average optical density of the region within the selected object is measured (step 523). Staining the blood smear for neutrophil alkaline phosphatase activity causes the average optical density of the neutrophil to increase. Thus, average optical density can be graded against a known scale, indicating a level of alkaline phosphatase within neutrophils. Data representing the results of the measurements for each object are then saved (step 525), for example to an ASCII file as noted above. When the ASCII file is found to contain the results for 100 neutrophils, then processing is completed (step 527). However, if data on fewer than 100 neutrophils have been stored in the ASCII file, then additional processing is required (steep 527). Therefore, the X-Y stage is then moved to the next adjacent optical field (step 529). Processing of this optical field begins with step 501, as discussed above. When N optical fields have been processed, then control returns to the processing loop (FIG. 4, step 409).

Grading can be performed after any of the program terminations, by subsequently performing mathematical operations on the stored data. For example, the data for 100 neutrophils can be averaged and compared to a threshold, as follows. The optical density of the red blood cells is defined as a baseline. The absolute optical density of the neutrophils is then calculated by deducting the optical density of the baseline from the obtained optical density value of each neutrophil. A final total score is obtained by averaging the calculated values from 100 neutrophils. This can be performed in a spreadsheet program or any other convenient calculating program. If fewer than 100 neutrophils have been measured, then this information should be reported along with the result, so as to flag potentially inaccurate or incomplete readings. The number of neutrophils or other objects to be measured, and the mathematical processing of the data prior to comparison with the predetermined scale can be varied to suit the requirements for implementing various assays which measure the level of an intracellular analyte.

In the case of detecting a Down syndrome pregnancy, a threshold is set to an absolute optical density equal to an appropriate multiple of the absolute optical density associated with a normal pregnancy. The appropriate multiple is selected in the same manner as setting a MoM threshold was conventionally done.

Similarly, an appropriate threshold of alkaline phosphatase-based optical density may be set, suitable for detection of preleukemic states. The manner of setting of such a threshold is similar to that conventionally done by those skilled in the art of diagnosing preleukemic states.

The automated assay of the described embodiment of the present invention takes about 10 minutes to perform using a manually operated X-Y stage. Using an automated X-Y stage cuts the time to perform the assay to about 5 to 4 minutes.

The present invention has been described in connection with a particular embodiment thereof. Various modifications and extensions thereof which should suggest themselves to those of ordinary skill in the art are contemplated as falling within the scope of the present invention, which is limited only by the claims appended hereto.

What is claimed is:

1. A method for determining the level of a target substance in a plurality of cells from a cell-containing sample, the method comprising the steps of: treating the plurality of cells to make a presence of the target substance optically detectable;
   placing the plurality of cells in an optical path of an image detector;
   obtaining an image of an optical field including at least one cell as an array of points having optical density values;
   filtering the obtained image to moderate optical density values of those points in the image having extreme optical density values;
   selecting image objects within the filtered image conforming to a defined parameter set; and
   calculating the average optical density of those points which are within the selected image objects taking into account a background optical density.

2. A method as recited in claim 1, wherein the step of filtering further comprises the step of closing filtering.

3. A method as recited in claim 1, wherein the step of filtering further comprises the steps of:
   dilation filtering; and
   erosion filtering.

4. A method as recited in claim 1, further comprising the steps of:
   defining the parameter set to include a minimum object area;
   defining the parameter set to include a range of roundness;
   defining the parameter set to include a minimum density; and
   defining the parameter set to include a smoothing factor.

5. A method as recited in claim 1, wherein the step of treating the plurality of cells further comprises:
   supporting the plurality of cells from the cell-containing sample on a support; and
   applying a reagent for optically indicating the presence of the target substance to the plurality of cells.

6. A method for determining the level of alkaline phosphatase in a plurality of cells of a cell-containing sample, the method comprising the steps of:
   treating the plurality of cells to make a presence of alkaline phosphatase optically detectable;
   placing the treated plurality of cells in an optical path of an image detector to permit detection in an optical field by the image detector of at least one neutrophil;
   obtaining an image of the optical field as an array of points having optical density values;
   filtering the obtained image to moderate optical density values of those points in the image having extreme optical density values;
   obtaining the optical density at points throughout the filtered image;
   defining a parameter set within which a neutrophil fits;
   selecting neutrophils in accordance with the defined parameter set; and
   calculating the optical densities of the selected neutrophils.

7. A method for detecting a Down syndrome pregnancy by determining the level of alkaline phosphatase in a plurality of cells of a cell-containing sample, the method comprising the steps of:
   treating the plurality of cells to make a presence of alkaline phosphatase optically detectable;
   placing treated plurality of cells in an optical path of an image detector to permit detection in an optical field by the image detector of at least one neutrophil;
   obtaining an image of the optical field as an array of points having optical density values;
   filtering the obtained image to moderate optical density values of those points in the image having extreme optical density values;
   obtaining the optical density at points throughout the filtered image;
   defining a parameter set within which a neutrophil fits;
   selecting neutrophils in accordance with the defined parameter set;
   calculating an average optical density of the selected neutrophils; and
   comparing the average optical density of the selected neutrophils to a control optical density, thereby detecting a likelihood of a Down syndrome pregnancy when the average optical density exceeds the control optical density.

8. A level of detecting preleukemic states by determining the level of alkaline phosphatase in a plurality of cells of a cell-containing sample, the method comprising the steps of:
   treating the plurality of cells to make a presence of alkaline phosphatase optically detectable;
   placing the solid support in an optical path of an image detector to permit detection in an optical field by the image detector of at least one neutrophil;
   obtaining an image of the optical field as an array of points having optical density values;
   filtering the obtained image to moderate optical density values of those points in the image having extreme optical density values;
   obtaining the optical density at points throughout the filtered image;
   defining a parameter set within which a neutrophil fits;
   selecting neutrophils in accordance with the defined parameter set;
   calculating an average optical density of the selected neutrophils; and
   comparing the average optical density of the selected neutrophils to a control optical density, thereby detecting a likelihood of a preleukemic state when the average optical density is less than the control optical density.

* * * * *

UNITED STATES PATENT AND TRADEMARK OFFICE
CERTIFICATE OF CORRECTION

PATENT NO. : 5,352,613
DATED : October 4, 1994
INVENTOR(S) : Triantafillos P. Tafas and Petros Tsipouras It is certified that error appears in the above-indentified patent and that said Letters Patent is hereby corrected as shown below:

In the Claims:

Col. 12,
Claim 7, line 7, after the word "placing", add the word --the--.

Claim 8, line 1, delete the phrase "level of" and replace it with the phrase --method for--.

Column 2, line 44, delete the word "Pooh" and replace it with the word --Poon--.

Column 4, line 11, delete the word "phosphate" and replace it with the word --phosphatase--.

Column 5, line 48, delete the word "piperting" and replace it with the word --pipetting--.

Column 6, line 29, after "using", add the word --the--.

Column 6, line 67, delete the word "Macton" and replace it with the word --Macron--.

Column 7, line 3, delete the word "The" and replace it with the word --the--.

Column 7, line 6, after "up", add the word --to--.

UNITED STATES PATENT AND TRADEMARK OFFICE
CERTIFICATE OF CORRECTION

PATENT NO. : 5,352,613
DATED : October 4, 1994
INVENTOR(S) : Triantafillos P. Tafas, et al It is certified that error appears in the above-indentified patent and that said Letters Patent is hereby corrected as shown below:

Column 10, line 16, delete the word "steep" and replace it with the word --step--.

Signed and Sealed this

Fourth Day of April, 1995

Attest:

BRUCE LEHMAN

*Attesting Officer*       *Commissioner of Patents and Trademarks*